United States Patent
Ohmachi et al.

(10) Patent No.: US 9,861,687 B2
(45) Date of Patent: Jan. 9, 2018

(54) PROTEIN MATERIAL

(71) Applicant: MEGMILK SNOW BRAND CO., LTD., Hokkaido (JP)

(72) Inventors: Aiko Ohmachi, Saitama (JP); Hiroaki Matsuyama, Saitama (JP); Yoshikazu Morita, Saitama (JP); Yuko Ishida, Saitama (JP); Takayuki Nara, Saitama (JP); Ken Kato, Saitama (JP); Atsushi Serizawa, Sapporo (JP)

(73) Assignee: MEGMILK SNOW BRAND CO., LTD., Hokkaido (JP)

( * ) Notice: Subject to any disclaimer, the term of this patent is extended or adjusted under 35 U.S.C. 154(b) by 0 days.

(21) Appl. No.: 15/684,175

(22) Filed: Aug. 23, 2017

(65) Prior Publication Data

US 2017/0348399 A1 Dec. 7, 2017

Related U.S. Application Data

(63) Continuation of application No. 14/418,210, filed as application No. PCT/JP2012/069392 on Jul. 31, 2012, now abandoned.

(51) Int. Cl.

| | |
|---|---|
| *A61K 38/54* | (2006.01) |
| *A61K 38/46* | (2006.01) |
| *A23L 33/18* | (2016.01) |
| *A23L 33/17* | (2016.01) |
| *A23K 50/40* | (2016.01) |
| *A23K 20/189* | (2016.01) |
| *A23K 20/142* | (2016.01) |
| *A23K 20/147* | (2016.01) |
| *A23L 2/66* | (2006.01) |
| *A61K 38/44* | (2006.01) |
| *A61K 38/18* | (2006.01) |

(52) U.S. Cl.
CPC ............ *A61K 38/54* (2013.01); *A23K 20/142* (2016.05); *A23K 20/147* (2016.05); *A23K 20/189* (2016.05); *A23K 50/40* (2016.05); *A23L 2/66* (2013.01); *A23L 33/17* (2016.08); *A23L 33/18* (2016.08); *A61K 38/1891* (2013.01); *A61K 38/44* (2013.01); *A61K 38/465* (2013.01); *A23V 2002/00* (2013.01); *A23V 2200/00* (2013.01); *C12Y 111/01007* (2013.01); *C12Y 301/27* (2013.01)

(58) Field of Classification Search
None
See application file for complete search history.

(56) References Cited

U.S. PATENT DOCUMENTS

| | | | |
|---|---|---|---|
| 5,932,259 A | 8/1999 | Kato et al. | |
| 8,551,547 B2 | 10/2013 | Brown et al. | |
| 9,119,818 B2 | 9/2015 | McDonagh et al. | |
| 9,522,178 B2 | 12/2016 | Ohmachi et al. | |
| 2006/0228345 A1 | 10/2006 | Motouri et al. | |
| 2007/0253941 A1 | 11/2007 | Naidu et al. | |
| 2010/0136172 A1 | 6/2010 | Brown et al. | |
| 2010/0209412 A1 | 8/2010 | Motouri et al. | |
| 2011/0008361 A1* | 1/2011 | Bragger | A61K 35/20 424/157.1 |
| 2011/0151016 A1 | 6/2011 | McDonagh et al. | |
| 2011/0262422 A1 | 10/2011 | Cocks et al. | |
| 2014/0065161 A1 | 3/2014 | Bragger | |
| 2015/0182557 A1 | 7/2015 | Ohmachi et al. | |
| 2015/0297690 A1 | 10/2015 | Ohmachi et al. | |
| 2015/0343029 A1 | 12/2015 | Ohmachi et al. | |
| 2015/0343030 A1 | 12/2015 | Ohmachi et al. | |
| 2016/0015791 A1 | 1/2016 | McDonagh et al. | |

FOREIGN PATENT DOCUMENTS

| | | |
|---|---|---|
| CN | 1835766 | 9/2006 |
| CN | 101626693 | 1/2010 |
| CN | 102088995 | 6/2011 |
| CN | 102099050 | 6/2011 |
| JP | 8-151331 | 6/1996 |
| JP | 10-007585 | 1/1998 |
| JP | 2004-238320 | 8/2004 |
| JP | 2005-60321 | 3/2005 |
| JP | 2011-519960 | 7/2011 |
| RU | 2366294 | 10/2009 |
| WO | 2007/142542 | 12/2007 |

OTHER PUBLICATIONS

English Translation for JP 2004-238320, 15 pages, performed on Feb. 2017. (Year: 2017).*
English Translation for JP 10-007585, 22 pages, performed on Feb. 2017. (Year: 2017).*
International search report issued with respect to application No. PCT/JP2012/069392, dated Sep. 11, 2012.
Y. Morita et al., "Purifcation and identification of lactoperoxidase in milk basic proteins as an inhibitor of osteoclastogenesis", Journal of Dairy Science, 2011, vol. 94, No. 5, pp. 2270-2279.
International preliminary report on patentability issued with respect to application No. PCT/JP2012/069392, dated Feb. 3, 2015.
Serizawa, "Development of 'Milk Basic Protein, MBP®'—A Novel Functional Food Ingredient for Bone Health," *The Third Symposium on Pharmaceutical Food Science Abstracts*, S-06, pp. 33-36, 2009, along with an English-language abstract and partial translation.
Japanese Office Action issued in JP Patent Application No. 2014-527849, dated Jun. 30, 2016, along with an English-language translation.
Search report issued with respect to application No. 11201500457R, dated Jul. 13, 2015.
Chinese Office Action issued in CN Patent Appl. No. 201280074984.7, dated Nov. 5, 2015.
Morita et al., "Identification of Angiogenin as the Osteoclastic Bone Resorption-Inhibitory Factor in Bovine Milk," *Bone*, vol. 42, No. 2, pp. 380-387 (Dec. 4, 2007).

(Continued)

*Primary Examiner* — Thane Underdahl
(74) *Attorney, Agent, or Firm* — Greenblum & Bernstein, P.L.C.

(57) ABSTRACT

The invention relates to a protein material includes angiogenin and/or angiogenin hydrolysate in an amount of 2 to 15 mg/100 mg, and lactoperoxidase and/or lactoperoxidase hydrolysate, in the mass ratio to angiogenin and/or angiogenin hydrolysate of 0.3 to 20.

7 Claims, No Drawings

(56) References Cited

OTHER PUBLICATIONS

Toba et al., "Milk Basic Protein: A Novel Protective Function of Milk Against Osteoporosis," *Bone*, vol. 27, No. 3, pp. 403-408 (Sep. 1, 2000).
"Composition of IDP," pp. 1-4 (Nov. 16, 2015).
Search Report issued by European Patent Office (EPO) in EPO Patent Application No. 12882508.0, dated Nov. 25, 2015.
"Osteo Equine," 1 page (Nov. 17, 2013).
Office Action issued in Chinese Counterpart Patent Appl. No. 201280074984.7, dated May 24, 2016, along with an English translation thereof.
Komolova et al., "Milk Angiogenin"; Applied Biochemistry and Microbiology; vol. 38, No. 3, XP055363270; Jan. 1, 2002; pp. 199-204.
Koksal et al., "An Important Milk Enzyme: Lactoperoxidase"; Milk Proteins—From Structure to Biological Propertied and Health Aspects, Chapter 7, InTech, XP055363418; Sep. 7, 2016; pp. 141-156.
European Office Action issued in Counterpart Patent Appl. No. 12 882 508.0, dated Apr. 18, 2017.
Partial English-language translation of JP 2005-060321 (Mar. 10, 2005).

\* cited by examiner

PROTEIN MATERIAL

This application is a Continuation of U.S. patent application Ser. No. 14/418,210, which is the National Stage of International Patent Application No. PCT/JP2012/069392, filed Jul. 31, 2012. The disclosures of each of application Ser. No. 14/418,210 and PCT/JP2012/069392 are expressly incorporated by reference herein in their entireties.

TECHNICAL FIELD

This invention relates to a novel protein material, and a drug, food, drink, or feed that includes the protein material and is useful for prevention and treatment of bone diseases. The protein material has functions of promoting osteoblast proliferation, and suppressing osteoclast differentiation and osteoclastic bone resorption. Therefore, the protein material is useful for prevention and treatment of various bone diseases, such as osteoporosis, fracture, rheumatism, and arthritis.

BACKGROUND ART

In recent years, various bone diseases, such as osteoporosis, fracture, and backache have increased on a global basis along with aging of society and the like, and have become a serious social problem. These diseases are caused by insufficient calcium intake, depression of calcium absorption ability, hormone imbalance after menopause, and the like. It is considered that increase the body bone mass as much as possible by activating the osteoblast and bone formation from the early stage of life, and increase the maximum bone mass and the bone strength (bone density+ bone quality) is effective in preventing various bone diseases, such as osteoporosis, fracture, and backache. Note that the term "bone quality" refers to the bone microstructure, metabolic turnover, microfracture, and calcification. It is thought that various bone diseases, such as osteoporosis, fracture, and backache may be prevented by suppressing osteoclastic bone resorption. Bones are repeatedly resorbed and formed in a balanced manner (remodeling). However, various bone diseases, such as osteoporosis, fracture, and backache may occur when bone resorption exceeds bone formation due to a change in hormone balance after menopause, and the like. Therefore, bones can be strengthened by suppressing osteoclastic bone resorption and maintaining the bone strength at a constant level.

In view of the above situation, a drug, food, drink, feed, or the like, in which a calcium salt, such as calcium carbonate, calcium phosphate, or calcium lactate or a natural calcium product, such as whey calcium, bovine bone powder, or eggshell is added individually, has been administered in order to strengthen bones. A drug, food, drink, feed, or the like that contains such a calcium product together with a substance having a calcium absorption-promoting effect, such as casein phosphopeptide or oligosaccharide has also been used to strengthen bones. However, the calcium absorption rate is 50% or less when a food or drink that contains a calcium salt or a natural calcium product is administered, and the large part of the calcium administered may be discharged from the body without being absorbed. Moreover, even if calcium is absorbed into the body, it does not necessarily exhibit the bone metabolism-improving effect or a bone-strengthening effect, since the affinity to bones may differ according to its form or the type of nutritional ingredient administered together. An estrogen product, an active vitamin $D_3$ product, a vitamin $K_2$ product, a bisphosphonate product, a calcitonin product, and the like have been known as a drug for treating osteoporosis or strengthening bones, and new drugs such as an anti-RANKL antibody have been also developed. However, these drugs may have side effects such as buzzing in the ear, a headache, or loss of appetite. Moreover, the above substances are in a situation that they cannot be added to a food or drink at present from the viewpoint of safety, cost, and the like. Therefore, in light of the nature of various bone diseases, such as osteoporosis, fracture, and backache, development of such a bone-strengthening agent, food, drink, or feed that can be administered orally for a long time, increases the bone strength by promoting bone formation and suppressing bone resorption, and may be expected to have the effect of preventing or treating the various bone diseases has been desired.

There are several food materials that intends to improve the bone strength, for example, it has been reported that a basic protein derived from milk or a peptide fraction of an enzymatically degraded product thereof exhibits osteoblast proliferation activity, osteoclastic bone resorption suppression activity, and thus a bone-strengthening effect (see Patent Document 1). It has also been reported that angiogenin and lactoperoxidase, contained in a basic protein fraction derived from milk, independently have a function to improve the bone metabolism (see Patent Documents 2 to 4).

PRIOR-ART DOCUMENT

Patent Document

[Patent Document 1] JP-A-H08-151331
[Patent Document 2] JP-A-H10-7585
[Patent Document 3] JP-A-2004-238320
[Patent Document 4] JP-A-2005-60321

SUMMARY OF THE INVENTION

Problems to be Solved by the Invention

The invention relates to provide a novel protein material that is safe, promotes osteoblast proliferation while suppressing osteoclast differentiation and osteoclastic bone resorption by administering daily, and thus can strengthen bones.

The invention relates to provide a bone-strengthening drug, food, drink, or feed that is useful for prevention and treatment of various bone diseases, such as osteoporosis, fracture, rheumatism, and arthritis by administering orally.

Means for Solving the Problems

The inventors have found that the effects of effectively promoting osteoblast proliferation, and suppressing osteoclast differentiation and osteoclastic bone resorption can be obtained by administering a protein material that includes angiogenin and/or angiogenin hydrolysate in a specific amount, and further includes lactoperoxidase and/or lactoperoxidase hydrolysate in a specific mass ratio with respect to angiogenin and/or angiogenin hydrolysate. This finding has led to the completion of the invention.

Specifically, the invention includes following aspects:

(1) A protein material including: angiogenin and/or angiogenin hydrolysate in an amount of 2 to 15 mg/100 mg and lactoperoxidase and/or lactoperoxidase hydrolysate in the mass ratio to the angiogenin and/or angiogenin hydrolysate of 0.3 to 20.

(2) A food, drink, or feed including the protein material according to (1).

(3) A bone-strengthening agent including the protein material according to (1) as an active ingredient.

(4) A method of strengthening bones including administering the protein material according to (I) in amount of 5 mg/day or more.

(5) A method of preparing the protein material according to (1), including the following steps of 1) to 3):
1) preparing angiogenin and/or angiogenin hydrolysate;
2) preparing lactoperoxidase and/or lactoperoxidase hydrolysate; and
3) mixing the lactoperoxidase and/or lactoperoxidase hydrolysate according to above 2) and the angiogenin and/or angiogenin hydrolysate according to above 1) in the mass ratio to the angiogenin and/or angiogenin hydrolysate of 0.3 to 20.

(6) A method of producing the protein material according to (1), including a step of extracting a fraction containing angiogenin and/or angiogenin hydrolysate and lactoperoxidase and/or lactoperoxidase hydrolysate from milk and/or a material derived from milk in the mass ratio to the angiogenin and/or the angiogenin hydrolysate of 0.3 to 20.

(7) The method according to (6), further including another step of enzymatically degrading the angiogenin and/or the lactoperoxidase contained in the fraction.

Effects of the Invention

The protein material of the invention exhibits a remarkable bone-strengthening effect through the function of promoting osteoblast proliferation, and suppressing osteoclast differentiation and osteoclastic bone resorption. The drug, food, drink, or feed of the invention strengthens bones, and is useful for prevention and treatment of various bone diseases, such as osteoporosis, fracture, rheumatism, and arthritis.

EMBODIMENTS FOR CARRYING OUT THE INVENTION

A protein material of the invention is characterized in that the protein material includes angiogenin and/or angiogenin hydrolysate in a specific amount, and further includes lactoperoxidase and/or lactoperoxidase hydrolysate in a specific mass ratio with respect to angiogenin and/or angiogenin hydrolysate.

The protein material of the invention may be a mixture obtained by mixing a fraction containing angiogenin and/or angiogenin hydrolysate and a fraction containing lactoperoxidase and/or lactoperoxidase hydrolysate in a specific mass ratio, a material prepared by directly extracting a fraction containing angiogenin and/or angiogenin hydrolysate and lactoperoxidase and/or lactoperoxidase hydrolysate in a specific mass ratio from milk or a material derived from milk, such as skim milk or whey, or the like. The protein material of the invention may also include a material prepared by enzymatically degrading angiogenin and/or lactoperoxidase.

When preparing the protein material of the invention by mixing a fraction containing angiogenin and/or angiogenin hydrolysate and a fraction containing lactoperoxidase and/or lactoperoxidase hydrolysate, a fraction prepared from milk of a mammal, such as human, cow, buffalo, goat, or sheep, a fraction produced by genetic engineering, a fraction purified from blood or an internal organ, or the like may be used as the fraction containing angiogenin and/or angiogenin hydrolysate and the fraction containing lactoperoxidase and/or lactoperoxidase hydrolysate. A commercially available purified angiogenin or lactoperoxidase reagent may also be used. In this case, the protein material of the invention may be prepared by adjusting the mass ratio of lactoperoxidase and/or lactoperoxidase hydrolysate to angiogenin and/or angiogenin hydrolysate.

A product obtained by enzymatically degrading the above fraction containing angiogenin, the angiogenin reagent, the fraction containing lactoperoxidase, the lactoperoxidase reagent, or the like using one or more proteases may be used as angiogenin hydrolysate or lactoperoxidase hydrolysate.

When preparing the protein material of the invention by directly extracting a fraction which contains angiogenin and/or angiogenin hydrolysate and lactoperoxidase and/or lactoperoxidase hydrolysate in a specific mass ratio from milk or a material derived from milk, such as skim milk or whey, for example, milk or a material derived from milk may be brought into contact with a cation-exchange resin, and then milk-derived proteins adsorbed on the resin may be eluted at a salt concentration of 0.1 to 2.0 M, desalted and concentrated using a reverse osmosis membrane, an electrodialysis membrane, an ultrafiltration membrane, a microfiltration membrane, or the like, after that optionally subjected to limited degradation to a molecular weight of 8000 or less using a protease, such as trypsin, pancreatin, chymotrypsin, pepsin, papain, kallikrein, cathepsin, thermolysis, or V8 protease, When subjecting to limited degradation using a protease, it is preferable that the lower limit of the molecular weight is 500 or more. The protein material thus obtained may be dried by freeze-drying, spray drying, or the like.

When subjecting the protein material of the invention to LC/MS/MS analysis, after subjecting to modification and limited degradation under reducing condition using a digestive enzyme in the usual manner in order to carry out a proteome analysis of the protein material, it was confirmed that the protein material contained at least one of protein such as αs1-casein, αs2-casein, β-casein, or κ-casein, and proteolysis product thereof other than angiogenin and/or angiogenin hydrolysate and lactoperoxidase and/or lactoperoxidase hydrolysate.

The protein material of the invention includes angiogenin and/or angiogenin hydrolysate in an amount of 2 to 15 mg/100 mg, and includes lactoperoxidase and/or lactoperoxidase hydrolysate in the mass ratio of 0.3 to 20 to angiogenin and/or angiogenin hydrolysate.

As shown in the test examples described below, when the mass ratio of lactoperoxidase and/or lactoperoxidase hydrolysate to angiogenin and/or angiogenin hydrolysate is 0.3 to 20, the bone-strengthening effect can be obtained more effectively than the case of administering angiogenin and/or angiogenin hydrolysate or lactoperoxidase and/or Iactoperoxidase hydrolysate separately.

Note that, for reference only, the content of angiogenin and/or angiogenin hydrolysate in cow milk is about 0.001%, and the mass ratio of lactoperoxidase and/or lactoperoxidase hydrolysate to angiogenin and/or angiogenin hydrolysate in cow milk is about 20. The content of angiogenin and/or angiogenin hydrolysate in a whey protein concentrate (WPC) is about 0.1%, and the mass ratio of lactoperoxidase and/or lactoperoxidase hydrolysate to angiogenin and/or angiogenin hydrolysate in a whey protein concentrate is about 30.

The protein material of the invention may be prepared as a bone-strengthening agent by appropriately adding the protein material as an active ingredient. The protein material of the invention may be used directly as a bone-strengthening agent. When formulating as a bone-strengthening agent, it may be possible to mix a raw material or the like that is usually used for drugs, food, drink, and feed, such as a saccharide, a lipid, a protein, a vitamin, a mineral, or a flavor, and it may be also possible to formulate into a powdered drug, granules, a tablet, a capsule, a drinkable preparation, or the like in the usual manner. The protein material of the invention may be used together with another ingredient that also exhibits a bone-strengthening effect, such as calcium, vitamin D, vitamin K, or isoflavone.

The protein material of the invention can strengthen bones when administered orally in an amount of 5 mg or more per kg of body weight, as shown in the animal experiments described below. Since the intake for this experimental animal corresponds to the intake for adults in terms of blood drug concentration (see Mitsuyoshi Nakajima (1993), "Yakkou Hyoka Vol. 8", Hirokawa-Shoten Ltd., pp. 2-18), it is expected that the bone-strengthening effect is obtained, and especially various bone diseases, such as osteoporosis, fracture, rheumatism, and arthritis can be prevented or treated by ingesting the protein material of the invention in an amount of 5 mg/day or more per an adult. Therefore, when mixing to a bone-strengthening agent or the like, the protein material may be added thereto so as to ingest the above necessary amount.

The protein material of the invention may be added to a normal food or drink, such as yogurt, beverage, wafer, or dessert). In this case, the protein material of the invention is preferably added in an amount of 0.25 to 1000 mg per 100 g of the food or drink depending on the form of the food or drink. It is expected that the bone-strengthening effect can be obtained by keeping the above mixing amount. The protein material of the invention may also be added to a feed, such as livestock feed or pet food to prepare a bone-strengthening feed. In this case, it is preferable to add the protein material of the invention in an amount of 0.25 to 1000 mg per 100 g of the feed.

When the protein material of the invention is prepared and used in the form of a drug, food, drink, or feed, the protein material of the invention may be used by suspending or dissolving in deionized water, and mixing with stirring. The stirring/mixing conditions are not particularly limited as long as the protein material is uniformly mixed. It is also possible to mix with stirring using an ultra-disperser, a TK-hornomixer, or the like.

The solution of the protein material may optionally be desalted or concentrated using a reverse osmosis membrane or the like, or freeze-dried so that the solution can be easily used for a drug, food, drink, or feed.

Notably, it was confirmed that the protein material of the invention maintains the bone-strengthening activity even when the protein material is subjected to sterilization treatment that is commonly used in the production of a drug, food, drink, or feed. The protein material may be subjected to dry-heat sterilization when the protein material is used as a powder. The protein material of the invention may be used for a drug, food, drink, or feed in various forms, such as liquid, gel, powder, or granular.

The invention is further described below in more detail by way of reference examples, examples, and test examples. Note that the following examples are intended for illustration purposes only, and should not be construed as limiting the invention.

REFERENCE EXAMPLE 1

Preparation (1) of Angiogenin Fraction

A column filled with 30 kg of cation-exchange resin (Sulfonated Chitopearl; manufactured by Fuji Spinning Co., Ltd.) was thoroughly washed with deionized water, and 1000 liters of unpasteurized skim milk (pH 6.7) was then applied to the column. After thoroughly washing the column with deionized water, the absorbed protein was eluted with a linear gradient of 0.1 to 2.0 M sodium chloride. The elution fraction containing angiogenin was fractionated using an S-Sepharose cation-exchange chromatography (manufactured by Amersham Bioscientific), and the resulted angiogenin-containing fraction was heat-treated at 90° C. for 10 minutes, and centrifuged to remove a precipitate. The angiogenin-containing fraction was further subjected to gel filtration chromatography (column: Superose 12). The eluate obtained was desalted using a reverse osmosis membrane, and the desalted eluate was freeze-dried to obtain 16.5 g of an angiogenin fraction having an angiogenin purity of 90%. These successive operations were repeated 30 times.

REFERENCE EXAMPLE 2

Preparation (2) of Angiogenin Fraction

A column filled with 10 kg of Heparin Sepharose (manufactured by GE Healthcare) was thoroughly washed with deionized water, and 1000 liters of unpasteurized skim milk (pH 6.7) was then applied to the column. After thoroughly washing the column with a 0.6 M sodium chloride solution, the absorbed protein was eluted with a 1.5 M sodium chloride solution. The eluate was desalted using a reverse osmosis membrane, and the desalted eluate was freeze-dried to obtain 32 g of an angiogenin fraction having an angiogenin purity of 2%. The above successive operations were repeated 50 times.

REFERENCE EXAMPLE 3

Preparation of Lactoperoxidase Fraction

A column (diameter: 5 cm, height: 30 cm) filled with 600 g of cation-exchange resin (Sulfonated Chitopearl; manufactured by Fuji Spinning Co., Ltd.) was thoroughly washed with deionized water, and 360 liters of unpasteurized skim milk (pH 6.7) was applied to the column at a flow rate of 25 ml/min. After thoroughly washing the column with deionized water, the absorbed protein was eluted with a 0.02 M carbonate buffer (pH 7.0) containing 2.0 M sodium chloride. The eluted fraction, containing lactoperoxidase was adsorbed on an S-Sepharose FF column (manufactured by Amersham Bioscientific), and the column was thoroughly washed with deionized water. After equilibration with a 10 mM phosphate buffer (pH 7.0), the adsorbed fraction was eluted with a linear gradient of 0 to 2.0 M sodium chloride to collect a fraction containing lactoperoxidase. The fraction was subjected to gel filtration chromatography using a HiLoad 16/60 Superdex 75 pg (manufactured by Amersham Bioscientific). The eluate obtained was desalted using a reverse osmosis membrane, and freeze-dried to obtain 27 g of a lactoperoxidase fraction having a lactoperoxidase purity of 90%. These successive operations were repeated 25 times.

EXAMPLE 1

Zero point five nine milligrams (0.59 mg) of the angiogenin fraction obtained in Reference Example 1, 98.58 mg of the angiogenin fraction obtained in Reference Example 2, and 0.83 mg of the lactoperoxidase fraction obtained in Reference Example 3 were mixed to prepare a protein material (example product 1), in which the content of angiogenin and/or angiogenin hydrolysate was 2.5 mg/100 mg, and the mass ratio of lactoperoxidase and/or lactoperoxidase hydrolysate to angiogenin and/or angiogenin hydrolysate was 0.3.

EXAMPLE 2

Zero point seven three milligrams (0.73 mg) of the angiogenin fraction obtained in Reference Example 1, 92.33 mg of the angiogenin fraction obtained in Reference Example 2, and 6.94 mg of the lactoperoxidase fraction obtained in Reference Example 3 were mixed to prepare a protein material (example product 2), in which the content of angiogenin and/or angiogenin hydrolysate was 2.5 mg/100 mg, and the mass ratio of lactoperoxidase and/or lactoperoxidase hydrolysate to angiogenin and/or angiogenin hydrolysate was 2.5.

EXAMPLE 3

One point eight three milligrams (1.83 mg) of the angiogenin fraction obtained in Reference Example 1, 42.61 mg of the angiogenin fraction obtained in Reference Example 2, and 55.56 mg of the lactoperoxidase fraction obtained in Reference Example 3 were mixed to prepare a protein material (example product 3), in which the content of angiogenin and/or angiogenin hydrolysate was 2.5 mg/100 mg, and the mass ratio of lactoperoxidase and/or lactoperoxidase hydrolysate to angiogenin and/or angiogenin hydrolysate was 20.

COMPARATIVE EXAMPLE 1

Zero point five seven (0.57 mg) of the angiogenin fraction obtained in Reference Example 1, 99.15 mg of the angiogenin fraction obtained in Reference Example 2, and 0.28 mg of the lactoperoxidase fraction obtained in Reference Example 3 were mixed to prepare a protein material (comparative example product 1), in which the content of angiogenin and/or angiogenin hydrolysate was 2.5 mg/100 mg, and the mass ratio of lactoperoxidase and/or lactoperoxidase hydrolysate to angiogenin and/or angiogenin hydrolysate was 0.1.

COMPARATIVE EXAMPLE 2

Two point zero eight milligrams (2.08 mg) of the angiogenin fraction obtained in Reference Example 1, 31.25 mg of the angiogenin fraction obtained in Reference Example 2, and 66.67 mg of the lactoperoxidase fraction obtained in Reference Example 3 were mixed to prepare a protein material (comparative example product 2), in which the content of angiogenin and/or angiogenin hydrolysate was 2.5 mg/100 mg, and the mass ratio of lactoperoxidase and/or lactoperoxidase hydrolysate to angiogenin and/or angiogenin hydrolysate was 24.

TEST EXAMPLE 1

The osteoblast proliferation effect, the suppressive effect on osteoclastic bone resorption, and the suppressive effect on osteoclast differentiation of the example products 1 to 3 and the comparative example products 1 and 2 were determined.

The osteoblast proliferation effect was determined as described below. An osteoblastic cell line (MC3T3-E1) was seeded on a 96-well cell culture plate at a density of $2 \times 10^3$ cells/welt, and cultured for 24 hours using an α-MEM medium (manufactured by GIBCO) supplemented with 10% fetal bovine serum (FBS). After the medium was completely removed, 90 µl of a FBS free α-MEM medium, and 10 µl of a solution containing any of the example products 1 to 3 and the comparative example products 1 and 2 is added to each well. The cells were further cultured for 24 hours. After the addition of bromodeoxyuridine (BrdU) which was included in the Cell Proliferation Kit (manufactured by GE Healthcare), the cells were cultured for 2 hours, and reacted with peroxidase-labelled anti-BrdU antibody. After the addition of 3,3',5,5'-tetramethylbenzidine (substrate), the osteoblast proliferation activity was determined by measuring the amount of BrdU introduced into the cells through measuring the absorbance at 450 nm. The osteoblast proliferation activity was determined to be positive when the absorbance at 450 nm was significantly higher than that of a group (control), in which none of the example products 1 to 3 and the comparative example products 1 and 2 were added to the medium.

The suppressive effect on osteoclastic bone resorption was determined as described below. The tibia and the thighbone were taken out from a rabbit (5 days old). After removing the soft tissue, these bones were mechanically chopped and the total bone marrow cells containing the osteoclasts were dispersed in an α-MEM medium supplemented with 5% FBS, and then seeded on the wells of a crystalline calcium phosphate plate (manufactured by Corning) at a density of $1 \times 10^6$ cells/well. The medium was completely removed at 2 hours after starting the culture, and 180 µl of an α-MEM medium supplemented with 5% FBS, and 20 µl of a solution containing any of the example products 1 to 3 and the comparative example products 1 and 2 was added to each well. The cells were cultured for 72 hours. After removing the cells by addition of a 5% sodium hypochlorite solution, resorption pits formed on the wells of the calcium phosphate plate were photographed using a stereoscopic microscope, and the area thereof was measured by image analysis to determine the suppressive effect on osteoclastic bone resorption (Takeshi Seno et al., "Manual of selected cultured cell lines for bioscience biotechnology", pp. 199-200, 1993). The suppressive activity against osteoclastic bone resorption was determined to be positive when the pit area was significantly smaller than that of a group (control), in which any of the example products 1 to 3 and the comparative example products 1 and 2 was not added to the medium.

The suppressive effect on osteoclast differentiation was determined as described below. The bone marrow cells collected from the thighbone of a ddy mouse (7 or 8 weeks old, male) were seeded on a 96-well plate at a density of $4 \times 10^4$ cells/well, and cultured in 200 µl of a α-MEM medium supplemented with 10% FBS and M-CSF (25 ng/ml) at 37° C. and 5% $CO_2$. After the medium was completely removed on 2 days after starting the culture 180 µl of a α-MEM medium supplemented with 10% FBS, RANKL (5 ng/ml) and M-CSF (25 ng/ml), and 20 µl of a solution containing any of the example products 1 to 3 and the comparative example products 1 and 2 was added to each well, and the cells were cultured under the condition of 37° C. and 5% $CO_2$ for 2 days. After changing the medium, the cells were further cultured for 1 day. At the completion of the culture, the culture solution was removed, washed with 1'BS, and treated with an acetone-ethanol (1:1) solution for 1 minute to fix the cells. After that, 1.5 mg/ml of a disodium p-nitrophenylphosphate-20 mM sodium tartrate-50 mM citrate buffer (pH 4.5) was added (100 µl/well), and reacted at room temperature for 30 minutes, and then, a 1 M sodium hydroxide solution (50 µl/well) was added to terminate the reaction. The absorbance at 405 nm was measured, and taken as an index of osteoclast differentiation/mutation. The suppressive activity against osteoclast differentiation was determined to be positive when the absorbance at 405 nm of group adding example products 1 to 3 or the comparative example products 1 or 2 was significantly lower than that of a group (control), in which any product of example products 1 to 3 and the comparative example products 1 and 2 was not added to the medium.

The results are shown in Table 1.

TABLE 1

|  | osteoblast proliferation activity | suppressive activity against osteoclastic bone resorption | suppressive activity against osteoclast differentiation |
|---|---|---|---|
| Example 1 | positive | positive | positive |
| Example 2 | positive | positive | positive |
| Example 3 | positive | positive | positive |
| Comparative example 1 | positive | positive | negative |
| Comparative example 2 | positive | negative | positive |

As shown in Table 1, the example products 1 to 3 which correspond to the protein material of the invention exhibited positive activity in all cell assays. The comparative example products 1 and 2 also exhibited positive activity in the some cell assays, but there were one cell assay that exhibited negative activity.

EXAMPLE 4

A column (diameter: 5 cm, height: 30 cm) filled with 600 g of cation-exchange resin (Sulfonated Chitopearl; manufactured by Fuji Spinning Co., Ltd.) was thoroughly washed with deionized water, and 40 liters of unpasteurized skim milk (pH 6.7) was applied to the column at a flow rate of 25 ml/min. After thoroughly washing the column with deionized water, proteins adsorbed on the resin were eluted using a 0.02 M carbonate buffer (pH 7.0) containing 0.78 M sodium chloride. The eluate was desalted using a reverse osmosis membrane, and the desalted eluate was freeze-dried to obtain 18 g of a powdery protein material (example product 4). The protein material contained angiogenin and/or angiogenin hydrolysate in an amount of 2 mg/100 mg, and the mass ratio of lactoperoxidase and/or lactoperoxidase hydrolysate to angiogenin and/or angiogenin hydrolysate was 18. The protein material may be used directly as a bone-strengthening agent or an active ingredient of a bone-strengthening agent. As a result of proteome analysis, it was found that the protein material contained degraded product of β-casein and degraded product of κ-casein.

EXAMPLE 5

A column (diameter: 20 cm, height: 100 cm) filled with 30 kg of cation-exchange resin (SP Toyopearl; manufactured by Tosoh Corporation) was thoroughly washed with deionized water, and 3 t of whey (pH 6.2) which was heat-sterilized at 75° C. for 15 minutes was applied to the column at a flow rate of 10 l/min. After thoroughly washing the column with deionized water, proteins adsorbed on the resin were eluted using a 0.1 M citrate buffer (pH 5.7) containing 0.68 M sodium chloride. The eluate was desalted using an electrodialysis membrane, and the desalted eluate was freeze-dried. The above successive operations were repeated 20 times to obtain 3.3 kg of a powdery protein material (example product 5). The protein material contained angiogenin and/or angiogenin hydrolysate in an amount of 15 mg/100 mg, and the mass ratio of lactoperoxidase and/or lactoperoxidase hydrolysate to angiogenin and/or angiogenin hydrolysate was 0.8. The protein material may be used directly as a bone-strengthening agent or an active ingredient of a bone-strengthening agent. As a result of proteome analysis, it was found that the protein material contained degraded products of $\alpha s1$-casein and κ-casein.

EXAMPLE 6

Four grams (4 g) of protein material of the example product 4 was dissolved in 800 ml of water. After the addition of pancreatin (manufactured by Sigma), which was a protease, at the final concentration of 0.02 wt %, and then the mixture was subjected to enzymatic treatment at 37° C. for 8 hours. After inactivating the protease through heat-treatment at 90° C. for 5 minutes, the mixture was freeze-dried to obtain 3.2 g of a protein material (example product 6). The protein material thus obtained contained angiogenin hydrolysate in an amount of 2.0 mg/100 mg, and the mass ratio of lactoperoxidase hydrolysate to angiogenin hydrolysate was 16, and the molecular weight of the protein material was 8000 or less. Therefore, the protein material may be used directly as a bone-strengthening agent or an active ingredient of a bone-strengthening agent. As a result of proteome analysis, it was found that the protein material contained degraded products of β-casein and κ-casein.

EXAMPLE 7

Four grams (4 g) of protein material of the example product 5 was dissolved in 800 ml of water. After the addition of trypsin (manufactured by Sigma), which was a protease, so as to obtain at the final concentration of 0.03 wt %, the mixture was subjected to enzymatic treatment at 37° C. for 8 hours. After inactivating the protease through heat-treatment at 90° C. for 5 minutes, the mixture was freeze-dried to obtain 3.0 g of a protein material (example product 7). The protein material thus obtained contained angiogenin hydrolysate in an amount of 14 mg/100 mg, and the mass ratio of lactoperoxidase hydrolysate to angiogenin hydrolysate in the protein material was 0.7, and the molecular weight of the protein material was 8000 or less. Therefore, the protein material may be used directly as a bone-strengthening agent or an active ingredient of a bone-strengthening agent. As a result of proteome analysis, it was found that the protein material contained degraded products of $\alpha s1$-casein and κ-casein.

COMPARATIVE EXAMPLE 3

Ten milligrams (10 mg) of the lactoperoxidase fraction obtained in Reference Example 3 and 100 mg of the protein material of the example product 4 were mixed to prepare a protein material (comparative example product 3), in which the content of angiogenin and/or angiogenin hydrolysate was 1.8 mg/100 mg, and the mass ratio of lactoperoxidase and/or lactoperoxidase hydrolysate to angiogenin and/or angiogenin hydrolysate was 22.5.

COMPARATIVE EXAMPLE 4

One gram (1 g) of the angiogenin fraction obtained in Reference Example 1 and 2 g of the protein material of the example product 5 were mixed and dissolved in 800 ml of water. After the addition of trypsin (manufactured by Sigma), which is a protease, at the final concentration of 0.02 wt %, the mixture was subjected to enzymatic treatment at 37° C. for 12 hours. After inactivating the protease through heat-treatment at 90° C. for 5 minutes, the mixture was freeze-dried to obtain 2.8 g of a protein material (comparative example product 4). The protein material thus obtained contained angiogenin hydrolysate in an amount of 39 mg/100 mg, and the mass ratio of lactoperoxidase hydrolysate to angiogenin hydrolysate was 0.2.

COMPARATIVE EXAMPLE 5

A column (diameter: 5 cm, height: 5 cm) filled with 100 g of cation-exchange resin (CM Sepharose FF; manufactured by GE Healthcare) was thoroughly washed with deionized water, and 40 liters of unpasteurized skim milk (pH 6.7) was applied to the column at a flow rate of 40 ml/min. After thoroughly washing the column with deionized water, proteins adsorbed on the resin were eluted using a 0.02 M carbonate buffer (pH 6.8) containing 0.98 M sodium chloride. The eluate was desalted using a reverse osmosis membrane, and the desalted eluate was freeze-dried to obtain 20 g of a powdery protein material (comparative example product 5). The protein material contained angiogenin and/or angiogenin hydrolysate in an amount of 1.5 mg/100 mg, and the mass ratio of lactoperoxidase and/or lactoperoxidase hydrolysate to angiogenin and/or angiogenin hydrolysate was 30.

TEST EXAMPLE 2

Each bone-strengthening effect of the example products 4 and 5 and the comparative example products 3 and 5 were determined by animal experiments. C3H/HeJ mice (5 weeks old, male) were used for the animal experiments. After 1 week acclimation, the mice were divided into five groups (6 mice/group). The mice were orally administered the example products 4 or 5 or the comparative example products 3 or 5 in an amount of 5 mg per 1 kg of body weight once a day for 4 weeks using a tube. The control group was not administrated any example products 4 and 5 and the comparative example products 3 and 5 were not administered. After completion of administration (fourth week), the bone density of the right tibia of each mouse was measured using a micro-CT (manufactured by Rigaku Corporation). The results are shown in Table 2.

TABLE 2

| | Bone density (mg/cm³) |
|---|---|
| Control group | 1300 ± 10 |
| Example product 4 | 1327 ± 11 |
| Example product 5 | 1332 ± 12 |
| Comparative example product 3 | 1301 ± 10 |
| Comparative example product 5 | 1304 ± 9 |

As shown in Table 2, the groups that were orally administered the example product 4 or 5 that were the protein material of the invention showed a significant increase in bone density as compared with the control group and the groups that were orally administered the comparative example product 3 or 5.

TEST EXAMPLE 3

Each bone-strengthening effect of the example products 6 and 7 and the comparative example products 4 and 5 was determined by animal experiments. Forty-eight SD rats (51 weeks old, female) were used for the animal experiments. The rats were divided into six groups (8 rats/group). Five groups underwent ovariectomy, and the remaining one group was subjected to sham surgery. After a 4-week recovery period, the rats underwent ovariectomy were orally administered the example products 6 or 7 or the comparative example products 4 or 5) in an amount of 5 mg per 1 kg of rat weight once a day for 16 weeks using a tube. The control group was not administrated any example products 6 and 7 and the comparative example products 4 and 5. After a 4-week recovery period, the rats underwent sham surgery were fed for 16 weeks in the same manner as the control group. After completion of administration (sixteenth week), the bone density of the right tibia of each rat was measured using a micro-CT (manufactured by Rigaku Corporation). The results are shown in Table 3.

TABLE 3

| | Bone density (mg/cm³) |
|---|---|
| Control group | 551 ± 10 |
| Sham surgery group | 602 ± 9 |
| Example product 6 | 598 ± 11 |
| Example product 7 | 594 ± 12 |
| Comparative example product 4 | 557 ± 13 |
| Comparative example product 5 | 555 ± 11 |

As shown in Table 3, the groups that were orally administered the example product 6 or 7 that was the protein material of the invention showed a significant increase in bone density as compared with the control group and the groups that were orally administered the comparative example product 4 or 5. Moreover, the bone density approached that of the sham surgery group.

EXAMPLE 8

Preparation of Bone-Strengthening Liquid Nutritional Supplement

Five grams (5 g) of the protein material of the example product 4 was dissolved in 4995 g of deionized water. The solution was stirred at 6000 rpm for 30 minutes using a TK-homomixer (TK ROBO MICS; manufactured by Tokushu Kika Kogyo co., ltd.) to obtain a solution containing the example product 4 in an amount of 100 mg/100 g. Then, 4.0 kg of casein, 5.0 kg of a soybean protein, 1.0 kg of fish oil, 3.0 kg of perilla oil, 18.0 kg of dextrin, 6.0 kg of a mineral mixture, 1.95 kg of a vitamin mixture, 2.0 kg of an emulsifying agent, 4.0 kg of a stabilizer, and 0.05 kg of essence were added to 5.0 kg of the solution. The mixture was charged in a retort pouch (200 ml) and sterilized at 121° C. for 20 minutes using a retort sterilizer (class-1 pressure vessel, RCS-4CRTGN; manufactured by Hisaka Works, Ltd.) to produce 50 kg of a bone-strengthening liquid nutrient composition. Any precipitation was observed, and no abnormal flavor was felt in the bone-strengthening liquid nutrient composition thus obtained.

EXAMPLE 9

Preparation of Bone-Strengthening Gel-Like Food

Two grams (2 g) of the protein material of the example product 5 was dissolved in 708 g of deionized water. The solution was stirred and mixed using an ultra-disperser (ULTRA-TURRAX T-25; manufactured by IKA Japan) at 9500 rpm for 30 minutes. 40 g sorbitol, 2 g of a sour agent, 2 g of essence, 5 g of pectin, 5 g of a whey protein concentrate, 1 g of calcium lactate, and 235 g of deionized water were added to the solution. After stirring and mixing, the mixture was charged into a 200 ml cheer pack, and sterilized at 85° C. for 20 minutes, and the pack was sealed to obtain five packs (200 g) of a bone-strengthening gel-like food. Any precipitation was observed, and no abnormal flavor was felt in the bone-strengthening gel-like food thus obtained.

EXAMPLE 10

Preparation of Bone-Strengthening Drink

Two grams (2 g) of an acidifier was dissolved in 706 g of deionized water, and 4 g of the protein material of the example product 6 was dissolved in the solution. The solution was stirred and mixed using an ultra-disperser (ULTRA-TURRAX T-25; manufactured by IKA Japan) at 9500 rpm for 30 minutes. After the addition of 100 g of maltitol, 20 g of reduced starch syrup, 2 g of essence, and 166 g of deionized water, the mixture was charged into a 100 ml glass bottle. After sterilized at 95° C. for 15 seconds, the bottle was closely sealed to obtain ten bottles (100 ml) of a bone-strengthening drink. Any precipitation was observed, and no abnormal flavor was felt in the bone-strengthening drink thus obtained

EXAMPLE 11

Preparation of Bone-Strengthening Feed

Two kilograms (2 kg) of the protein material of the example product 7 was dissolved in 95 kg of deionized water. The solution was stirred and mixed using a TK-homomixer (MARK II 160; manufactured by PRIMIX Corporation) at 3600 rpm for 40 minutes to obtain a solution containing the example product 7 in an amount of 2 g/100 g. Then, 12 kg of soybean meal, 14 kg of powdered skim milk, 4 kg of soybean oil, 2 kg of corn oil, 23.2 kg of palm oil, 14 kg of corn starch, 9 kg of flour, 2 kg of bran, 5 kg of a vitamin mixture, 2.8 kg of cellulose, and 2 kg of a mineral mixture were added to 10 kg of the solution. The mixture was sterilized at 120° C. for 4 minutes to obtain 100 kg of a bone-strengthening dog food.

EXAMPLE 12

Preparation of Bone-Strengthening Agent (Tablet)

The raw materials were mixed in the ratio shown in Table 4. Then, 1 g of the mixture was formed and tableted in the usual manner to prepare a bone-strengthening agent.

TABLE 4

| Hydrous crystalline glucose | 92.5% (wt %) |
| Protein material (example product 1) | 1.0% |
| Mineral mixture | 5.0% |
| Sugar ester | 1.0% |
| Essence | 0.5% |

The invention claimed is:

1. A protein material comprising angiogenin and/or angiogenin hydrolysate in an amount of 2 to 15 mg/100 mg and lactoperoxidase and/or lactoperoxidase hydrolysate in the mass ratio to the angiogenin and/or angiogenin hydrolysate of 0.3:1 to 20:1.

2. A food, drink, or feed comprising the protein material according to claim 1.

3. A bone-strengthening agent comprising the protein material according to claim 1 as an active ingredient.

4. A method of strengthening bones comprising administering the protein material according to claim 1 in an amount of 5 mg/day or more.

5. A method of preparing the protein material according to claim 1, comprising following steps 1) to 3):
   1) preparing angiogenin and/or angiogenin hydrolysate;
   2) preparing lactoperoxidase and/or lactoperoxidase hydrolysate; and
   3) mixing the lactoperoxidase and/or lactoperoxidase hydrolysate according to above 2) and the angiogenin and/or angiogenin hydrolysate according to above 1) in the mass ratio to the angiogenin and/or angiogenin hydrolysate of 0.3:1 to 20:1.

6. A method of preparing the protein material according to claim 1, comprising a step of extracting a fraction containing angiogenin and/or angiogenin hydrolysate and lactoperoxidase and/or lactoperoxidase hydrolysate from milk and/or a material derived from milk in the mass ratio to the angiogenin and/or the angiogenin hydrolysate of 0.3:1 to 20:1.

7. The method according to claim 6, further comprising another step of enzymatically degrading the angiogenin and/or the lactoperoxidase contained in the fraction.

* * * * *